United States Patent
Nishino et al.

(10) Patent No.: US 10,570,432 B2
(45) Date of Patent: Feb. 25, 2020

(54) METHOD FOR PRODUCING SACCHARIFIED SOLUTION BY ENZYMATIC METHOD USING CELLULOSE-TYPE BIOMASS AS RAW MATERIAL

(71) Applicant: KAWASAKI JUKOGYO KABUSHIKI KAISHA, Kobe-shi, Hyogo (JP)

(72) Inventors: Takashi Nishino, Suita (JP); Noriaki Izumi, Kobe (JP); Hironori Tajiri, Kobe (JP); Hiromasa Kusuda, Kobe (JP); Shoji Tsujita, Itami (JP); Manabu Masamoto, Kobe (JP)

(73) Assignee: KAWASAKI JUKOGYO KABUSHIKI KAISHA, Kobe-Shi (JP)

( * ) Notice: Subject to any disclaimer, the term of this patent is extended or adjusted under 35 U.S.C. 154(b) by 0 days.

(21) Appl. No.: 16/076,629

(22) PCT Filed: Feb. 3, 2017

(86) PCT No.: PCT/JP2017/004085
§ 371 (c)(1),
(2) Date: Aug. 8, 2018

(87) PCT Pub. No.: WO2017/138462
PCT Pub. Date: Aug. 17, 2017

(65) Prior Publication Data
US 2019/0048377 A1  Feb. 14, 2019

(30) Foreign Application Priority Data
Feb. 8, 2016 (JP) ................... 2016-022058

(51) Int. Cl.
| C12P 19/14 | (2006.01) |
| C13K 1/02 | (2006.01) |
| C12N 9/42 | (2006.01) |
| C12P 7/10 | (2006.01) |
| D21C 1/02 | (2006.01) |

(52) U.S. Cl.
CPC ............ *C12P 19/14* (2013.01); *C12N 9/2437* (2013.01); *C12P 7/10* (2013.01); *C13K 1/02* (2013.01); *D21C 1/02* (2013.01); *C12Y 302/01004* (2013.01)

(58) Field of Classification Search
None
See application file for complete search history.

(56) References Cited

U.S. PATENT DOCUMENTS

| 2012/0009642 A1 | 1/2012 | Suzuki et al. |
| 2012/0055466 A1 | 3/2012 | Cotti Comettini et al. |
| 2012/0107920 A1* | 5/2012 | Taneda ............... C12P 19/14 435/276 |
| 2012/0164694 A1 | 6/2012 | Taneda et al. |
| 2013/0052696 A1* | 2/2013 | Ueyama ............... C12P 7/10 435/99 |
| 2016/0312319 A1 | 10/2016 | Kusuda et al. |

FOREIGN PATENT DOCUMENTS

| EP | 2 942 386 A1 | 11/2015 |
| WO | 2011/142290 A1 | 11/2011 |
| WO | 2012/004894 A1 | 1/2012 |
| WO | 2015/098070 A1 | 7/2015 |

OTHER PUBLICATIONS

Jul. 1, 2019 Extended European Search Report Issued in European Patent Application No. 17750185.5.
Roche, Christine M., et al. "Particle Concentration and Yield Stress of Biomass Slurries During Enzymatic Hydrolysis at High-Solids Loadings." Biotechnology and Bioengineering, vol. 104, No. 2., Wiley Periodicals, Inc., Oct. 1, 2009.

* cited by examiner

*Primary Examiner* — Heidi Reese
(74) *Attorney, Agent, or Firm* — Oliff PLC

(57) ABSTRACT

A method for producing a saccharified solution making it possible that while the concentration of a solid in a reactor is kept high at an initial stage of hydrolyzing a cellulose contained in a biomass with an enzyme, the biomass is earlier solubilized to be made into a slurry form. In the method, at an initial stage of mixing an aqueous solution containing a biomass pulverized in a reactor, the aqueous solution is poured into reactor, and then pulverized biomass is supplied thereinto step by step while content in reactor is stirred. A final solid concentration in reactor is set into the range of 15 to 30% both inclusive by mass. The reactor's bottom plane is made into a conical or mirror plate form. At least in upper and lower parts of the reactor's inside, plural stirring fans having a long rotation radius are located to stir content in reactor.

16 Claims, 2 Drawing Sheets

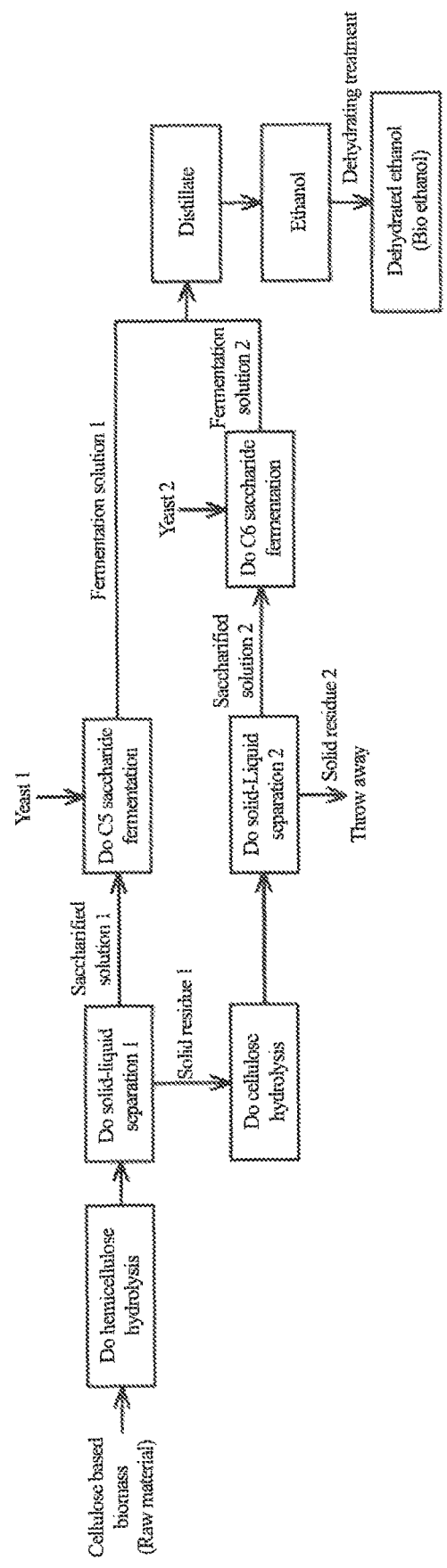
[Fig. 1]

[Fig. 2]
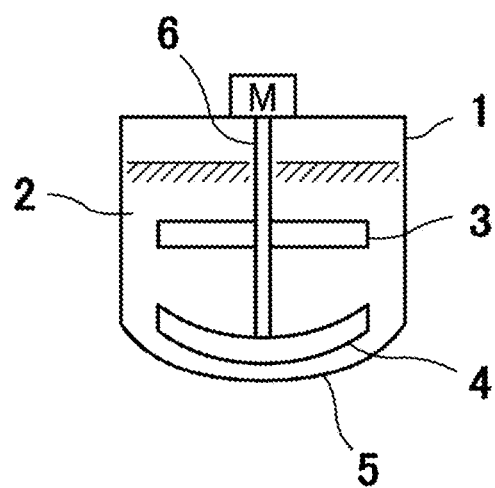
(a)
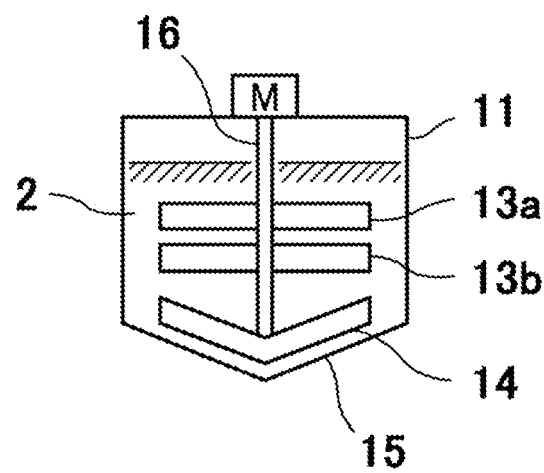
(b)

METHOD FOR PRODUCING SACCHARIFIED SOLUTION BY ENZYMATIC METHOD USING CELLULOSE-TYPE BIOMASS AS RAW MATERIAL

TECHNICAL FIELD

The present invention relates to a method of using a hydrolase to hydrolyze a cellulose-type biomass to produce a saccharified solution, this method being used to produce a biochemical such as ethanol (bio ethanol) or polylactic acid from saccharides by a fermentation means such as alcohol fermentation or lactic acid fermentation.

BACKGROUND ART

As an example of using biomass energy, an attempt has been made for yielding ethanol by decomposing a cellulose or hemicellulose, which is a main component of plants, to produce a saccharified solution and then fermenting the resultant saccharide into alcohol. In the attempt, it has been planned to use the resultant ethanol for fuel and make a partial blend of ethanol mainly into a fuel for automobiles, or use a fuel alternative for gasoline.

In recent years, the following technique has also been industrially performed: a technique of decomposing a cellulose or hemicellulose, supplying the resultant saccharified solution to lactic acid fermentation to produce L-lactic acid, and then polymerizing this acid to produce polylactic acid, which is a bio-base polymer species. Attention has been paid to polylactic acid as a biodegradable plastic material.

Plants include, as main components thereof, any cellulose (polymer made from glucose, which is a C6 monosaccharide having 6 carbon atoms), any hemicellulose (polymer made from a C6 monosaccharide, and a C5 monosaccharide having 5 carbon atoms), lignin, and starch. Ethanol is produced by a fermentation effect of microorganisms, such as yeast, using as a raw material a C5 monosaccharide, a C6 monosaccharide, an oligosaccharide which is a complex of these monosaccharides, or some other saccharide as a raw material.

In order to decompose a cellulose-type biomass such as a cellulose or a hemicellulose into a saccharide, the following three methods are to be industrially used: a method 1) of hydrolyzing the biomass by the oxidizing-power of a strong acid such as sulfuric acid, a method 2) of decomposing the biomass by an enzyme, and a method 3) of using the oxidizing power of supercritical water or subcritical water. Out of these methods, the enzyme decomposition method 2) has a drawback of being longer in decomposition period than the other decomposition methods, but has advantages of being low in production-facility costs, and running costs, being capable of attaining a normal-temperature and normal-pressure treatment, and not causing an excessive decomposition of saccharides.

Patent Literature 1 discloses that in the case of transferring a lignocellulose-type biomass subjected to lignin removal or swelling treatment into a reactor for enzyme saccharification reaction through, for example, a vessel for transfer, miscellaneous bacteria are unfavorably incorporated into the lignocellulose-type biomass, for example, at the time of the shift of the lignocellulose-type biomass into the vessel for transfer, and discloses that when the ligno-cellulose-type biomass, into which the miscellaneous bacteria are incorporated, is caused to react for saccharification through an enzyme, the produced saccharides are consumed with the incorporated miscellaneous bacteria.

In order to solve such problems, Patent Literature 1 discloses a method for treating a lignocellulose-type biomass, this method being a lignocellulose-based-biomass-treating method of pretreating the lignocellulose-type biomass in one reactor, shifting the biomass into different reactors, and saccharifying the biomass with an enzyme to yield a saccharified solution, and being characterized by including a pretreating step of pretreating the lignocellulose-type biomass in the reactor, which is a first reactor, to dissociate lignin from the lignocellulose-type biomass or swell the lignocellulose-type biomass to yield a first treated product, a first saccharifying treatment step of subjecting the first treated product yielded through the first treatment step partially to enzyme saccharification reaction in one of the different rectors, which is a second reactor, to yield a second treated product, a transferring step of transferring the second treated product yielded through the first saccharifying treatment step in the state of bringing this product into no contact with any external air, and a second saccharifying step of subjecting the second treated product transferred through the transferring step to enzyme saccharification reaction in one of the different rectors, which is a third reactor, to yield a saccharified solution.

As a method for hydrolyzing a cellulose in a very short period without requiring shearing, Patent Literature 2 discloses a method for hydrolyzing a lignocellulose biomass, including:

a step A of bringing a lignocellulose raw-material containing a biomass having a dry content and water into contact with at least one portion of a solvent containing water-soluble hydrolysis species, at least some of the water-soluble hydrolysis species being equal to water-soluble hydrolysis species that can be yielded by hydrolysis of the biomass in the raw-material, a step B of maintaining contact between the raw-material in raw-material flow and the solvent at a temperature ranging from 20 to 200° C. for a period of 5 minutes to 72 hours to produce a hydrolyzed product from the biomass in the raw-material.

As a method capable of increasing the production amount of saccharides made mainly of glucose even when enzyme saccharification reaction is conducted with a small quantity of an enzyme, Patent Literature 3 discloses a method of decomposing a cellulose and/or a hemicellulose with a cellulose hydrolase to produce saccharides made mainly of glucose, in which: the cellulose and/or the hemicellulose is/are mixed with an aqueous enzyme solution of the cellulose hydrolase; and subsequently while the mixture is stirred to mix the components with each other to satisfy the following relationship expression: $Y \leq -0.0125x^2 + 1.195x + 23.25$ in which Y represents stirring power ($W/m^3$) applied to the mixture of the cellulose and/or hemicellulose, and the aqueous enzyme solution, and X represents the addition ratio (w/v %) of the cellulose and/or the hemicellulose to the aqueous enzyme solution, an enzyme saccharification reaction is conducted for saccharifying the cellulose and/or the hemicellulose with the cellulose hydrolase.

CITATION LIST

Patent Literatures

PTL 1: WO 2011/142290
PTL 2: JP 2012-521778 A
PTL 3: JP 2012-139144 A

SUMMARY OF INVENTION

Technical Problem

When a cellulose in a biomass is hydrolyzed with a hydrolase such as cellulase, it is ideal to prepare an aqueous cellulose-containing solution the concentration of which is as high as possible, and hydrolyze the cellulose therewith to produce a saccharified solution high in concentration. However, when the solid concentration (biomass concentration) in the reacting vessel is made high at an initial stage of starting the hydrolysis of the cellulose, the content in the reaction vessel is not easily stirred since the viscosity of the content in the vessel is high. In the meantime, the use of a stirring device large in stirring power unfavorably increases costs for the installation and driving of the device.

When the stirring of the content in the reaction vessel is insufficient, the following period becomes long: a period for hydrolyzing the cellulose contained in the biomass partially to solubilize the biomass. Unless the cellulose is decomposed into some degree with the hydrolase to solubilize the biomass so that the mixture of the biomass and the aqueous cellulose hydrolase-containing solution is made into a slurry form to be made lower in viscosity, it is difficult to transfer, through a pipe and a pump, a slurry of the biomass into another large-sized vessel for hydrolyzing the cellulose.

When the hydrolysis of a biomass with an enzyme is industrially and continuously performed, it is more preferred to use a continuous treatment of using plural vessels to transfer a slurry of the biomass than a batch treatment. Patent Literatures 1 to 3 also each disclose a continuous treatment using plural vessel. However, these literatures never describe a treatment of solubilizing the biomass at an initial stage of starting the enzyme-hydrolysis of the cellulose.

An object of the present invention is to provide a method for producing a saccharified solution making it possible that while the concentration of a solid in a reactor is kept high at an initial stage of hydrolyzing a cellulose contained in a biomass with an enzyme, the biomass is earlier solubilized to be made into a slurry form.

Solution to Problem

In order to solve the above-mentioned problems, the inventors have repeatedly made eager investigations. As a result, the inventors have found out that at an initial stage of mixing a biomass pulverized in a reactor with an aqueous solution containing a cellulose hydrolase, by operations of pouring the aqueous solution into the reactor, and subsequently supplying the pulverized biomass thereinto step by step while the reaction system is stirred, the solubilization of the biomass can be finished in several hours or shorter even when a final solid concentration in the reactor is 15% or more by mass.

The inventors have also found out that by mixing the pulverized biomass with the aqueous solution containing the cellulose hydrolase, and further making a bottom plane of the reactor in which the biomass is to be solubilized in a conical form or mirror plate form, the biomass, which has been pulverized by means of a stirring device, and the aqueous solution can easily stirred. Furthermore, the inventors have found out that by locating plural stirring fans having a large rotation radius to at least the upper and the lower parts of the inside of the reactor, and stirring a content (aqueous solution containing the pulverized biomass and the hydrolase) in the reactor, the content in the reactor can be evenly stirred in the reactor. Thus, the present invention has been accomplished.

Specifically, the present invention is:

a method for producing a saccharified solution of hydrolyzing a cellulose-type biomass with enzyme to yield a saccharified solution, including:

a step A of decomposing a hemicellulose contained in the cellulose-type biomass by hot-water treatment or with a hemicellulose hydrolase, a step B of mixing a solid residue yielded by removing the hemicellulose with an aqueous solution containing a cellulose hydrolase in a reactor, adjusting the mixture to set a solid concentration therein into a range of 15 to 30% both inclusive by mass, and subsequently using a stirring device located in the reactor to stir the mixture to solubilize the solid residue, from which the hemicellulose has been removed, a step C of continuing cellulose hydrolysis reaction inside the reactor while stirring the mixture by the stirring device until the cellulose hydrolysis reaction inside the reactor is finished, and a step D of taking out a slurry of the mixture from the reactor after the hydrolysis reaction, in which in the step B, the aqueous solution containing the cellulose hydrolase is poured into the reactor, and subsequently the solid residue yielded through the step A, from which the hemicellulose has been removed, is supplied step by step into the reactor while a content in the reactor is stirred by the stirring device located in the reactor.

It is preferred that:

the step (C) is continued for a period of 5 minutes to 120 hours both inclusive to set the temperature of the content in the reactor into a range of 20 to 90° C. both inclusive.

It is preferred that:

the reactor has a bottom plane in a conical form or a mirror plate from; and the stirring device has:

a plurality of stirring fans at least in an upper part and a lower part of the reactor.

It is preferred that the stirring fans of the stirring device is selected from the group consisting of helical ribbons, double helical ribbons, Maxblends, inclined paddle fans, and anchor fans; and the stirring fans has a rotation speed of 0.5 to 5.0 m/second both inclusive as a circumferential speed thereof.

In the method for producing a saccharified solution of the present invention, it is also preferred that the step B and the step C are performed in different reactors, and after the step B is finished, a content is taken out from the reactor in which the step B has been performed, and a pump is used to supply the content into the reactor in which the step C is performed.

The method for producing a saccharified solution of the present invention may further includes:

after the step A, a step A1 of removing lignin contained in the cellulose-type biomass.

Advantageous Effects of Invention

The method for producing a saccharified solution of the present invention makes it possible that in a pro-stage of hydrolyzing of a cellulose contained in a pulverized biomass, a solubilizing treatment of the biomass is effectively conducted.

BRIEF DESCRIPTION OF DRAWINGS

FIG. 1 shows a basic flowchart of a process for producing a saccharified solution from a cellulose-type biomass by an enzymatic method.

FIG. 2 each illustrate a schematic structural view of a reactor suitable for performing a step B.

DESCRIPTION OF EMBODIMENTS

Referring appropriately to the drawings, embodiments of the present invention will be described. FIG. 1 shows a basic flowchart of a process for producing a saccharified solution from a cellulose-type biomass by an enzymatic method.

<Pre-Treatment Step>

Initially, a cellulose-type biomass (hereinafter referred to as a "biomass"), such as sugar cane, is roughly pulverized by means of a crusher or pulverizer. At this time, the biomass is preferably made into small pieces having an average dimeter of 30 to 50 mm or less (more preferably 10 mm or less). The roughly pulverized biomass is hydrolyzed with a solution of a metal hydroxide such as sodium hydroxide in ethanol water. By this hydrolyzing treatment, lignin contained in the bagasse is partially removed to improve the reactivity between the cellulose and hemicellulose, and the enzyme. An acid is used to neutralize the hydrolyzed biomass.

Instead of the hydrolysis with the metal hydroxide solution in ethanol water, a blasting machine may be used to conduct blasting treatment with water vapor (at 200 to 240° C. and 1.5 to 4 MPa for 1 to 15 minutes, preferably at 225 to 230° C. and 2.5 to 3 MPa for 1 to 5 minutes) to saccharify the hemicellulose component in the biomass. The biomass treated by the blasting machine (blasted product) contains a C5 based saccharified solution originating from the hemicellulose, fermentation hindering materials such as a sacharide-decomposed product and a lignin lysate, and a solid residue. For example, a filter press is used to subject this blasted product to solid-liquid separation to separate the product into a blasted liquid and the solid residue. When the solid residue is further washed appropriately with water, saccharides contained in the solid residue can be collected.

After the solid residue yielded by the blasting treatment is washed with water so that the saccharides and the lignin lysate are removed, the solid residue is immersed in ethanol water having an ethanol concentration of 30% or more, preferably 50% or more at ambient temperature for a period from 0.5 to 48 hours both inclusive, preferably from 1 to 24 hours both inclusive to dissolve and remove lignin, with which the cellulose is coated. After the immersion in ethanol, the solid residue is subjected to a mechanical de-ethanol treatment, or a de-ethanol treatment, for example, by heating or heating under reduced pressure. When ethanol water with a high concentration is used, the solid residue may be once washed with water and then subjected to de-ethanol treatment.

<Hydrolysis (Saccharification of Hemicellulose>

The hemicellulose contained in the cellulose-type biomass is hydrolyzed (or hot-water-treated) with high-temperature and high-pressure water, or decomposed with a hemicellulose hydrolase such as hemicellulase. When the hemicellulose is hydrolyzed with high-temperature and high-pressure water, the hemicellulose can be decomposed into saccharides (mainly, a C5 monosaccharide) when the temperature is from 140 to 180° C. both inclusive. In the case of a biomass in which the hemicellulose content is large, the resultant C5 monosaccharide is unfavorably decomposed excessively into an organic acid and others when the biomass is treated at high temperature. Thus, it is preferred to conduct the decomposing treatment under relatively mild conditions.

When the hemicellulose is hydrolyzed with high-temperature and high-pressure water, it is mentioned that preferred is also the addition of an acid, such as phosphoric acid or hydrochloric acid, as a catalyst into the system. Moreover, when the hemicellulose is hydrolyzed with hemicellulose hydrolase, a commercially available enzyme may be used, or a microorganism or the like that produces hemicellulase may be used.

<Solid-Liquid Separation 1>

After the hydrolysis of the hemicellulose is finished, the reaction system is subjected to solid-liquid separation 1 to separate the system into a solid residue 1 and a saccharified solution 1 (C5 saccharified solution).

<C5 Saccharide Fermentation>

Yeast is added to the saccharified solution 1 to yield an alcohol (fermentation liquid 1) by hemicellulose saccharide fermentation.

<Cellulose Hydrolysis (Saccharification)>

Water, and a cellulose hydrolase such as cellulase are added to the solid residue 1 to hydrolyze the cellulose contained in the solid residue 1. When the cellulose is hydrolyzed with the cellulose hydrolase, a commercially available enzyme may be used, or a microorganism or the like that produces cellulase may be used.

<Solid-Liquid Separation 2>

After the hydrolysis of the cellulose is finished, the present system is subjected to solid-liquid separation 2 to separate the system into a solid residue 2 and a saccharified solution 2 (C6 saccharified solution). The solid residue is optionally washed with water. The C6 saccharified solution is collected therefrom, and then the residue is disposed of.

<C6 Saccharide Fermentation>

Yeast is added to the saccharified solution 2 to yield an alcohol (fermentation liquid 2) by cellulose saccharide fermentation.

In FIG. 1, the C5 saccharide fermentation and the C6 saccharide fermentation are each independently performed. However, it is allowable to mix the saccharified solution 1 and the saccharified solution 2 with each other, and subject the mixed saccharified solution simultaneously to C5 saccharide fermentation and C6 saccharide fermentation.

<Distillation and Dehydration>

The alcohol-fermentation liquids (fermentation liquid 1 and the fermentation liquid 2) yielded by subjecting the C5 saccharified solution and C6 saccharified solution to alcohol fermentation are supplied to a distillation machine to yield ethanol by distillation. This liquid ethanol is dehydrated with a known ethanol dehydrating agent or by means of a dehydrating machine, and the resultant is forwarded as a commercial product (bio ethanol).

In FIG. 1, it is allowable to omit the solid-liquid separation 1 and the solid-liquid separation 2, and perform hemicellulose saccharide fermentation and cellulose saccharide fermentation in the state that the solid residue is incorporated in the system.

(Step A)

The following will describe each step in the method of the present invention for producing a saccharified solution. Initially, a cellulose-type biomass is roughly pulverized, and subsequently a hemicellulose contained therein is decomposed by hot-water treatment or with a hemicellulose hydrolase. After the step A is finished, a solid-liquid separating device is used to subject the resultant C5 saccharified solution and solid residue to solid-liquid separation.

(Step B)

Next, in a reactor, the solid residue, in which the hemicellulose has been removed, is mixed with an aqueous solution containing a cellulose hydrolase. The reactor has a bottom plane in a conical form or a mirror plate form. The material, the dimension, and other factors thereof may be appropriately selected in accordance with the amount of the cellulose-type biomass to be treated.

About the inside of the reactor, at least in an upper part and a lower part of its region which contacts its content plural stirring fans are located. It is more preferred that the proportion of the rotation diameter of the stirring fans to the inside diameter of the reactor is larger. It is ideal that the rotation radius thereof is 70% or more of the inside diameter of the reactor. The stirring fans of the stirring device preferably have helical ribbons, double helical ribbons, Maxblends, inclined paddle fans, or anchor fans. The stirring device may have the same plural stirring fan species, or may have different stirring fan species. The stirring fans preferably have a rotation speed of 0.5 to 5.0 m/second both inclusive as a circumferential speed thereof.

FIG. 2 each illustrate a schematic structural view of a reactor suitable for performing the step (B). A reactor 1 illustrated in FIG. 2(a) has stirring fans 3 and 4, and its bottom plane 5 is in a mirror plate form. A rotary axis 6 is rotated through a motor M located on the upper surface of the reactor 1. A reactor 11 illustrated in FIG. 2(b) has stirring fans 13a and 13b, and 14. The stirring fans 13a and 13b are the same stirring fan species. A bottom plane 15 of the reactor 11 is in a conical form. A rotary axis 16 is rotated through a motor M located on the upper surface of the reactor 11.

The aqueous solution containing the cellulose hydrolase is earlier supplied to the reactor, and subsequently the solid residue, from which the hemicellulose has been removed, is supplied thereto step by step. At this time, it is allowable to supply a required amount of water thereto, and then add and blend the cellulose hydrolase thereinto to prepare an aqueous solution of the cellulose hydrolase. The solid residue is gradually supplied to the reactor while the aqueous solution is stirred with the stirring fans of the stirring device. About the solid concentration in the reactor, a final solid concentration therein is adjusted into a range of 15 to 30% both inclusive by mass. Thereafter, the reaction system is stirred with the stirring fans of the stirring device for a period of 5 minutes to 12 hours both inclusive. By such a treatment, the solid residue (cellulose-type biomass), from which the hemicellulose has been removed, is solubilized. In the step B, it is preferred to adjust the temperature of the content in the reactor into a range of 20 to 90° C. both inclusive.

The step B can be continuously performed by: supplying the aqueous solution containing the cellulose hydrolase, and the solid residue, from which the hemicellulose has been removed, continuously supplied into the reactor to keep the solid concentration in a predetermined concentration range after the solid concentration in the content inside the reactor reaches a predetermined concentration (of 15 to 30% both inclusive by mass) to solubilize the cellulose-type biomass; taking out the amount of the solution that corresponds to the continuously supplied amount; and supplying the solution to the reactor in which the step C is to be performed.

Before the step B, it is preferred to perform a step A1 of subjecting the solid residue, from which the hemicellulose has been removed, to a hydrolyzing treatment with the above-mentioned solution in ethanol water or a blasting treatment with water vapor to remove lignin from the solid residue. The step A1 may be performed before the step A, or after the step A and before the step B.

(Step C)

Next, while the reaction system is stirred by the stirring device, the hydrolysis reaction is continued until a large proportion of the cellulose contained in the residue of the content (the mixture of the solid residue, from which the hemicellulose has been removed, and the aqueous solution containing the cellulose hydrolase) inside the reactor is turned to glucose (in other words, until the cellulose hydrolysis reaction of the content in the reactor is finished). In the step C, the reaction is continued over a period of 5 minutes to 120 hours both inclusive while the temperature of the content in the reactor is adjusted into the range of 20 to 90° C. both inclusive. Though the step C, the cellulose contained in the solid residue is hydrolyzed so that the content in the reactor is made into a slurry form.

(Step D)

After the step C is finished, the slurry is taken out from the reactor. The taken-out slurry is optionally subjected to solid-liquid separation to separate the slurry into a solid residue and a C6 saccharified solution. The C6 saccharified solution is independently kept, or mixed with the resultant C5 saccharified solution, and then this C5 saccharified solution, or the mixture is supplied to ethanol fermentation or lactic acid fermentation to be used as a raw material of bio ethanol or bio lactic acid.

The step B and the step C may be performed in a single reactor. It is however allowable to perform the step B and the step C in different vessels, pull out the content from the reactor in which the step B has been performed after the end of the step B, and then supply this content in the reactor in which the step C is performed by effect of a pump. The step C requires a longer period than the step B. Thus, when a large amount of a cellulose-type biomass is continuously treated, it is preferred to perform the step B and the step C in different reactors. In this case, the reactor in which the step C is performed is preferably made larger in size than that in which the step B is performed.

After the step C turns into a stationary state and the content is made into a slurry form, a shiny portion having a liquid amount corresponding to the volume of the aqueous solution which contains the cellulose-type biomass pulverized and supplied from the step B, and contains the cellulose hydrolase is taken out from the reactor in which the step C is being performed. In this way, a saccharified solution can be continuously produced while the solid concentration in the slurry in the step C is kept constant. The reactor in which the step B is performed may be small in size.

INDUSTRIAL APPLICABILITY

The method for producing a saccharified solution of the present invention is useful as a method for producing a sacchadrified solution in the field of a biochemical such as bio ethanol or bio lactic acid.

REFERENCE SINGS LIST 1,11 Reactors
2 Content in reactor
3 Stirring fan (upper stirring fan)

4 Stirring fan (lower stirring fan)
5 Mirror plate form bottom plane
6 Rotary axis of stirring device
13a Stirring fan (upper stirring fan)
13b Stirring fan (central stirring fan)
14 Stirring fan (lower stirring fan)
15 Conical bottom plane

The invention claimed is:

1. A method for producing a saccharified solution of hydrolyzing a cellulose-type biomass with an enzyme to yield a saccharified solution, comprising:
   a step A of decomposing a hemicellulose comprised in the cellulose-type biomass by hot-water treatment or with a hemicellulose hydrolase,
   a step B of mixing a solid residue yielded by removing the hemicellulose with an aqueous solution comprising a cellulose hydrolase in a reactor, adjusting the mixture to set a solid concentration therein into a range of 15 to 30% both inclusive by mass, and subsequently using a stirring device having a plurality of stirring fans located in the reactor to stir the mixture to solubilize the solid residue, from which the hemicellulose has been removed,
   a step C of continuing cellulose hydrolysis reaction inside the reactor while stirring the mixture by the stirring device until the cellulose hydrolysis reaction inside the reactor is finished, and
   a step D of taking out a slurry of the mixture from the reactor after the hydrolysis reaction,
   wherein in the step B,
   the aqueous solution comprising the cellulose hydrolase is poured into the reactor, and subsequently the solid residue yielded through the step A, from which the hemicellulose has been removed, is supplied step by step into the reactor while a content in the reactor is stirred by the stirring device located in the reactor.

2. The method for producing a saccharified solution according to claim 1, wherein the reactor is:
   a reactor having a bottom plane in a conical form or a mirror plate form; and
   the stirring device has:
   the plurality of stirring fans at least in an upper part and a lower part of the reactor.

3. The method for producing a saccharified solution according to claim 1, wherein the stirring fans of the stirring device are selected from the group consisting of helical ribbons, double helical ribbons, inclined paddle fans, and anchor fans; and
   the stirring fans have a rotation speed of 0.5 to 5.0 m/second both inclusive as a circumferential speed thereof.

4. The method for producing a saccharified solution according to claim 1, wherein the step B and the step C are performed in different reactors, and
   after the step B is finished, a content is taken out from the reactor in which the step B has been performed, and a pump is used to supply the content into the reactor in which the step C is performed.

5. The method for producing a saccharified solution according to claim 1, further comprising, before the step B, a step A1 of removing lignin comprised in the cellulose-type biomass.

6. The method for producing a saccharified solution according to claim 2, wherein the stirring fans of the stirring device are selected from the group consisting of helical ribbons, double helical ribbons, inclined paddle fans, and anchor fans; and
   the stirring fans have a rotation speed of 0.5 to 5.0 m/second both inclusive as a circumferential speed thereof.

7. The method for producing a saccharified solution according to claim 2, wherein the step B and the step C are performed in different reactors, and
   after the step B is finished, a content is taken out from the reactor in which the step B has been performed, and a pump is used to supply the content into the reactor in which the step C is performed.

8. The method for producing a saccharified solution according to claim 3, wherein the step B and the step C are performed in different reactors, and
   after the step B is finished, a content is taken out from the reactor in which the step B has been performed, and a pump is used to supply the content into the reactor in which the step C is performed.

9. The method for producing a saccharified solution according to claim 6, wherein the step B and the step C are performed in different reactors, and
   after the step B is finished, a content is taken out from the reactor in which the step B has been performed, and a pump is used to supply the content into the reactor in which the step C is performed.

10. The method for producing a saccharified solution according to claim 2, further comprising, before the step B, a step A1 of removing lignin comprised in the cellulose-type biomass.

11. The method for producing a saccharified solution according to claim 3, further comprising, before the step B, a step A1 of removing lignin comprised in the cellulose-type biomass.

12. The method for producing a saccharified solution according to claim 4, further comprising, before the step B, a step A1 of removing lignin comprised in the cellulose-type biomass.

13. The method for producing a saccharified solution according to claim 6, further comprising, before the step B, a step A1 of removing lignin comprised in the cellulose-type biomass.

14. The method for producing a saccharified solution according to claim 7, further comprising, before the step B, a step A1 of removing lignin comprised in the cellulose-type biomass.

15. The method for producing a saccharified solution according to claim 8, further comprising, before the step B, a step A1 of removing lignin comprised in the cellulose-type biomass.

16. The method for producing a saccharified solution according to claim 9, further comprising, before the step B, a step A1 of removing lignin comprised in the cellulose-type biomass.

* * * * *